United States Patent [19]
Suzuki et al.

[11] Patent Number: 4,733,001
[45] Date of Patent: Mar. 22, 1988

[54] METHOD FOR PREPARING A MIXTURE OF STEREOISOMERS OF α-CYANO-3-PHENOXYBENZYL ISOVALERATE ESTER DERIVATIVES HAVING A HIGHER INSECTICIDAL AND ACARICIDAL ACTIVITY

[75] Inventors: Yukio Suzuki; Masahiro Hayashi, both of Osaka; Kenzi Takuma, Nara, all of Japan

[73] Assignee: Sumitomo Chemical Company, Limited, Osaka, Japan

[21] Appl. No.: 267,982

[22] Filed: May 28, 1981

[30] Foreign Application Priority Data

May 28, 1980 [JP] Japan ................................ 55-71940

[51] Int. Cl.$^4$ .......................................... C07C 121/52
[52] U.S. Cl. .................................... 558/354; 558/398
[58] Field of Search .................. 260/465 D; 558/354, 558/398

[56] References Cited

U.S. PATENT DOCUMENTS

| 4,062,968 | 12/1977 | Fujimoto et al. | 424/308 |
| 4,176,195 | 11/1979 | Stoutamire | 424/304 |
| 4,238,406 | 12/1980 | Suzuki et al. | 260/465 D |
| 4,279,924 | 7/1981 | Suzuki et al. | 424/304 |
| 4,293,504 | 10/1981 | Suzuki et al. | 260/465 D |

FOREIGN PATENT DOCUMENTS

| 1549462 | 8/1969 | United Kingdom . |
| 2001964A | 2/1979 | United Kingdom . |
| 2041365A | 9/1980 | United Kingdom . |
| 2041366A | 9/1980 | United Kingdom . |

Primary Examiner—Anton H. Sutto
Attorney, Agent, or Firm—Sughrue, Mion, Zinn, Macpeak, and Seas

[57] ABSTRACT

A method for preparing a mixture of stereoisomers of α-cyano-3-phenoxybenzyl isovalerate ester derivatives, which is rich is an enantiomer pair of a compound having an (S)-configuration on both the acid and alcohol moieties and an enantiomer thereof having an (R)-configuration on both the acid and alcohol moieties.

34 Claims, 1 Drawing Figure

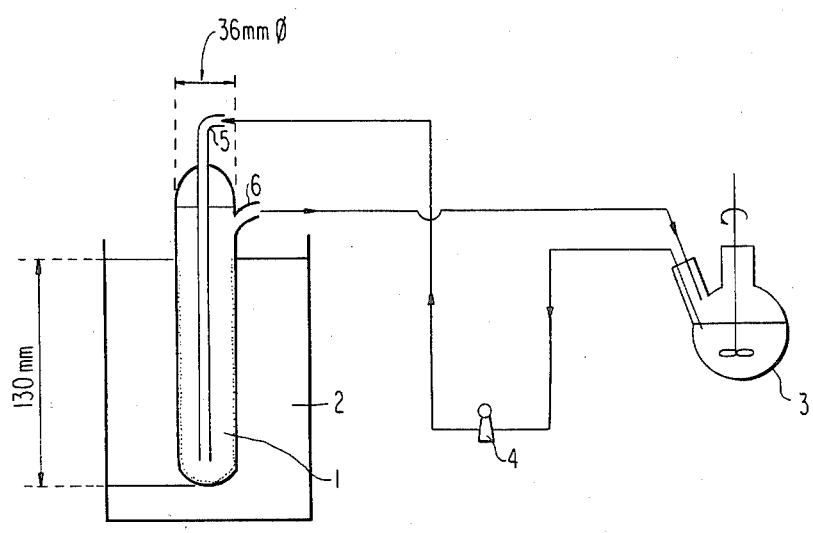

METHOD FOR PREPARING A MIXTURE OF STEREOISOMERS OF α-CYANO-3-PHENOXYBENZYL ISOVALERATE ESTER DERIVATIVES HAVING A HIGHER INSECTICIDAL AND ACARICIDAL ACTIVITY

This invention relates to a method for preparing a mixture of stereoisomers of α-cyano-3-phenoxybenzyl isovalerate ester derivatives of the formula (I):

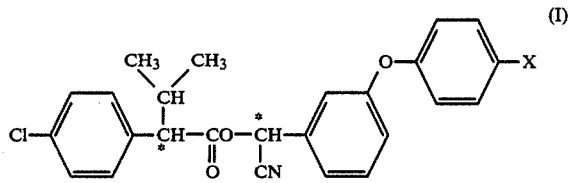

wherein X is a hydrogen atom or a fluorine atom, and * indicates an asymmetric carbon atom, which mixture is rich in an enantiomer pair of a compound of the formula (I) having an (S)-configuration on both the acid and alcohol moieties and its enantiomer. More particularly, it relates to a method for preparing said mixture, which comprises removing crystals of a compound of the formula (I) rich is other enantiomer pair of a compound of the formula (I) having an (S)-configuration on the acid moiety and an (R)-configuration on the alcohol moiety and it enantiomer, from the ester of the formula (I) which is a mixture of these enantiomer pairs.

α-Cyano-3-phenoxybenzyl 2-(4-chlorophenyl)isovalerate (hereinafter, this compound being referred to as "fenvalerate") and α-cyano-3-(4-fluorophenoxy)benzyl 2-(4-chlorophenyl)isovalerate (hereinafter, this compound being referred to as "p-F fenvalerate") are useful as insecticides and/or acaricides as disclosed in, for example, U.S. Pat. No. 4,062,968 and British Pat. No. 1,549,462. These esters have one asymmetric carbon atom on each of the acid and alcohol moieties.

These optical isomers are hereunder referred to as shown in Table 1 below.

TABLE 1

| | Abbreviations for Optical Isomers | | |
| --- | --- | --- | --- |
| | Acid Moiety | | |
| Alcohol Moiety | (S)-Configuration | Racemic | (R)-Configuration |
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

Combinations of the Aα-isomer and the Bβ-isomer and of the Aβ-isomer and the Bα-isomer are each in a relationship of enantiomer pair. The enantiomer pair of the Aα-isomer and the Bβ-isomer is herein referred to as a Y-isomer, and the enantiomer pair of the Aβ-isomer and the Bα-isomer as an X-isomer. An ester provided by the conventional method is a mixture comprising substantially equal amounts of four isomers, i.e., "racemate".

According to the disclosure of U.S. Pat. No. 4,238,406, the insecticidal and/or acaricidal efficacy of the Y-isomer of fenvalerate is about twice as high as that of racemic fenvalerate ("racemate") [the ratio of X-isomer to Y-isomer is about 1:1 (hereinafter unless otherwise stated, the racemic fenvalerate refers to fenvalerate of this composition)], and the Y-isomer or the ester rich in the Y-isomer can be obtained by crystallizing the Y-isomer out of racemic fenvalerate in the presence or absence of a base. As described above, it is well known that the Y-isomer of fenvalerate forms a crystal (m.p. 40° C.). Further, GB 2,001,964A sets forth that both the Aα-isomer and the Bβ-isomer of fenvalerate form a crystal (m.p. 57.9° C. for the Aα-isomer; 59.6° C. for the Bβ-isomer). But, nothing has hitherto been known about crystallization of the Aβ-isomer, Bα-isomer and X-isomer of fenvalerate.

In addition, with respect to p-F fenvalerate, it is disclosed in GB No. 2,041,366A that the insecticidal and/or acaricidal efficacy of the Y-isomer is about twice as high as that of racemic p-F fenvalerate ("racemate") [the meaning for the term "racemic" is the same as that in fenvalerate], and the Y-isomer or the ester rich in the Y-isomer can be obtained by crystallizing the Y-isomer out of racemic p-F fenvalerate. Further, it is also known that the Aα-isomer of p-F fenvalerate forms a crystal as disclosed in GB No. 2,041,365A. But, nothing has hitherto been known about crystallization of the Aβ-isomer, Bα-isomer and X-isomer of p-F fenvalerate.

As the result of further extensive studies on these esters, the present inventors reached novel findings that the X-isomer of fenvalerate crystallizes (m.p. 63°–66° C.), and also that even the racemic fenvalerate, only recognized as a viscous liquid until now, can crystallize (m.p. 37.0°–53.6° C.), and that the X-isomer of p-F fenvalerate also crystallizes (m.p. 76.5°–78.0° C.).

The present inventors made further studies on the basis of this novel fact, and found that by crystallizing the X-isomer of the ester rich in the X-isomer of the formula (I) from the racemic ester thereof and removing the resulting crystals, the ester rich in the Y-isomer can be obtained from the mother liquor. After a further investigation, the present inventors attained to the present invention.

The ester of the formula (I) which is rich in the Y-isomer and the ester of the formula (I) which is rich in the X-isomer are hereunder referred to as a Y-rich and an X-rich, respectively.

This invention provides a method in which the X-rich is removed as crystals from the ester of the formula (I) which is a mixture of the X-isomer and the Y-isomer and then, the Y-rich is obtained from the mother liquor, more preferably a method in which the X-rich is removed by crystallizing it out of a solution of the ester of the formula (I) which is a mixture of the X-isomer and the Y-isomer in the presence of a crystalline X-isomer or an X-rich and then, the Y-rich is obtained from the mother liquor.

In the methods described in U.S. Pat. No. 4,238,406 and GB No. 2,041,366A, the crystallization of the Y-isomer proceeds so extremely slowly that a long period of time is taken for completion of the crystallization even by adding large amounts of seed crystals of Y-isomer. In the method of the present invention, however, the crystallization of the X-rich proceeds so rapidly that it is completed in approximately several hours. This method is, therefore, more advantageous from the industrial viewpoint.

The X-rich separated from the racemic ester as also described in U.S. Pat. No. 4,238,406 and GB No. 2,041,366A can be returned to the "racemate" (epimerization), an approximately 1:1 mixture of the X-isomer and the Y-isomer, by bringing it into contact with a basic catalyst. Consequently, the Y-rich can be obtained approximately quantitatively from the racemic ester by repeated cycles of the crystallization and the epimerization.

The present invention will be illustrated in more detail hereinafter.

The ratio of the X-isomer to the Y-isomer present in the starting ester is preferably within a range of about 35/65 to about 65/35. The ester as the starting material may be of any form of liquid and solid. It is more favorable that both the acid and alcohol moieties of the starting ester are in a racemic form, but they need not always be a complete racemate.

The crystallization of the X-rich is preferably carried out in a solvent because the starting ester in a liquid form is viscous at the crystallization temperature of the X-rich. Suitable examples of the solvent which can be used include alcohols such as lower alcohols having 1 to 4 carbon atoms (e.g., methanol, ethanol, n-propanol, isopropanol, n-butanol, etc.), aliphatic hydrocarbons (e.g., pentane, heptane, hexane, petroleum ether, ligroin, etc.), alicyclic hydrocarbons (e.g., cyclohexane, methylcyclohexane, etc.), mixtures containing two or more of these solvents, and mixed solvents containing at least one of these solvents. Suitable examples of the mixed solvent which can be used are mixtures of at least one of the alcohols, aliphatic hydrocarbons, alicyclic hydrocarbons and mixtures of two or more of these solvents, with aromatic hydrocarbons (e.g., toluene, benzene, xylene, etc.). But, the solvent used in the present invention is not limited to these illustrated solvents. The amount of the solvent is generally about 0.5 to 10 times the weight of the ester used as the starting material.

The epimerization of this ester, which may occur when the alcohol or a mixed solvent containing the same is used as a solvent, can be avoided by the addition of a portion of acidic substance (e.g., acetic acid, hydrogen chloride, sulfuric acid, etc.).

The crystallization can be carried out in the presence of a crystalline X-isomer or an X-rich. Generally, it is carried out by dissolving the starting ester in a solvent and adding the foregoing crystal as a seed crystal at a temperature at which the crystallization takes place. But, the addition of the seed crystal is not necessary when the crystal is already contained in the crystallization system without being completely dissolved or melted. The crystallization of the X-rich can be carried out batchwisely, continuously or semi-continuously. When the crystallization is carried out continuously or semi-continuously, the seeding with crystals may be effected only at the initiation of crystallization of the X-rich.

This invention may be effected in the following manner as one example of the operation: the solution of the racemic ester is passed through a unit where the seed crystals of the X-isomer or the Y-rich are held and which unit is kept at the temperature at which the crystallization of the X-rich takes place, whereby the X-rich is precipitated in the unit to give a solution of the Y-rich.

When the starting ester is of almost solid form, mere washing or partial dissolving of the ester with a solvent enables the Y-rich to be obtained from the washings.

A temperature at which the crystallization is carried out is preferably 40° C. or less, more preferably −30° C. to 30° C. The precipitated X-rich is then separated from the mother liquor by a usual manner to separate the solid from the liquid such as filtration, decantation, centrifugation or the like. The Y-rich is thus recovered from the mother liquor.

The Y-isomer can be obtained from the Y-rich thus-obtained, if necessary, by recrystallization or other means.

The method of this invention is hereunder described in greater detail by reference to the following reference examples and examples.

In the following reference examples and examples, the ratio of X-isomer to Y-isomer was analyzed by gas chromatography. The analytical conditions were as follows:
Tube: 3 mm$\phi$×3.0 m tube packed with Chromosorb AW-DMCS coated with 10% silicone DC QF-1
Analytical Temperature: 245° C.
Injection Temperature: 250° C.
Nitrogen Pressure: 2.0 kg/cm$^2$.

In the following reference examples and examples, unless otherwise stated, fenvalerate, p-F fenvalerate, fenvalerate X, p-F fenvalerate X, fenvalerate Y and p-F fenvalerate Y mean racemates in both on the acid and alcohol moieties, and the ratios of X-isomer to Y-isomer in fenvalerate and p-F fenvalerate were 50:50, respectively, unless otherwise stated.

REFERENCE EXAMPLE 1

810 mg of fenvalerate was dissolved in hexane, and the solution was adsorbed on a silica gel column (Lobar Column Lichroprep Si 60, Size B, a trademark of Merk Co.) and then eluted with a hexane/ethyl acetate (100/1 by volume) mixed solvent. Fractions, from which the Y-isomer was hardly detectable by gas chromatography, were combined and concentrated to obtain 212 mg of the X-isomer. This X-isomer was dissolved in 1 cc of heptane, and the solution was allowed to stand, in a tightly sealed condition, for a week in a refrigerator (about 0° C.) to provide crystals which were then vacuum-dried to give X-isomer crystals (m.p. 63.0°–66.0° C.).

REFERENCE EXAMPLE 2

700 g of p-F fenvalerate was dissolved in hexane, and the solution was adsorbed on a silica gel column (Lobar Column Lichroprep Si 60, Size B) and eluted with a hexane/ethyl acetate (80:1 by volume) mixed solvent. Fractions of X-isomer which were eluted during the gas chromatography were combined and concentrated to obtain 190 mg of the X-isomer. To this X-isomer of p-F fenvalerate were added the crystals of X-isomer of fenvalerate obtained in Reference Example 1, and the X-isomer of p-F fenvalerate was solidified (m.p. 76.5°–78° C.).

EXAMPLE 1

50 g of fenvalerate was dissolved in 250 g of heptane, and after adding thereto as a seed crystal 1 mg of X-isomer crystals of fenvalerate at room temperature (20°–23° C.), the solution was stirred for 5 hours as it was. The precipitated crystals were filtered to give 14.80 g of an X-rich (X-isomer/Y-isomer=70.3/29.7). The mother liquor was concentrated to give a Y-rich (X-isomer/Y-isomer=41.0/59.0).

EXAMPLE 2

100 g of fenvalerate (X-isomer/Y-isomer=53.2/46.8) was dissolved in 200 g of methanol, and after adding thereto as a seed crystal 1 mg of X-isomer crystals of fenvalerate at room temperature (20°–23° C.), the solution was stirred for 5 hours as it was. The precipitated crystals were removed by filtration, and the mother liquor was concentrated to give 65.02 g of a Y-rich (X-isomer/Y-isomer=38.7/61.3).

EXAMPLE 3

50 g of fenvalerate (X-isomer/Y-isomer=53.2/46.8) was dissolved in 50 g of methanol, and the solution was cooled to 5° to 7° C. To the solution was added as a seed crystal 1 mg of X-isomer crystals of fenvalerate, and the resulting solution was stirred for 4 hours at the same temperature. The precipitated crystals were removed by filtration, and the mother liquor was concentrated to give 14.78 g of a Y-rich (X-isomer/Y-isomer=22.6/77.4).

REFERENCE EXAMPLE 3

To 100 g of liquid-form fenvalerate was added 100 g of heptane, followed by stirring at room temperature (20°-23° C.). One hour after the stirring, seed crystals of X-isomer and Y-isomer of fenvalerate were added thereto, followed by stirring for 16 hours at the same temperature. A nitrogen stream was passed through the system to evaporate most of heptane in 5 hours. The remaining semi-solid product was vacuum-dried to obtain solid-form fenvalerate (m.p. 37.0°-53.6° C.).

EXAMPLE 4

To 7 g of solid-form fenvalerate obtained in Reference Example 3 was added 7 g of methanol at room temperature (20°-23° C.), followed by stirring at the same temperature. 5.5 hours after the stirring, the crystals were removed by filtration, and the mother liquor was concentrated to give 3.03 g of a Y-rich (X-isomer/Y-isomer=34.5/65.5).

EXAMPLE 5

100 g of fenvalerate (X-isomer/Y-isomer=53.2/46.8) was dissolved in 200 g of methanol, and the solution was cooled to −18° C. To the solution was added 1 mg of X-rich crystals of fenvalerate obtained in Example 1, and the resulting solution was stirred for 5 hours at the same temperature. The precipitated crystals were removed by filtration, and the mother liquor was concentrated to give 33.58 g of a Y-rich (X-isomer/Y-isomer=23.6/76.4).

EXAMPLE 6

100 g of fenvalerate (X-isomer/Y-isomer=53.2/46.8) was dissolved in 200 g of isopropyl alcohol, and after adding thereto 1 mg of crystal-form fenvalerate, the solution was stirred for 6 hours at room temperature (20°-23° C.). The precipitated crystals were removed by filtration, and the mother liquor was concentrated to give 52.53 g of a Y-rich (X-isomer/Y-isomer=33.8/66.2).

EXAMPLE 7

To 7 g of solid-form fenvalerate obtained in Reference Example 3 was added 7 g of methanol and dissolved at 37° C. (at that time, no crystals remained in appearance). The solution was then cooled to 24° C. and stirred for 6 hours. The precipitated crystals were removed by filtration, and the mother liquor was concentrated to give 4.87 g of a Y-rich (X-isomer/Y-isomer=40.2/59.8).

EXAMPLE 8

100 g of fenvalerate (X-isomer/Y-isomer=53.2/46.8) was dissolved in a mixed solvent comprising 117 g of heptane, 13 g of toluene and 70 g of methanol, and the solution was cooled to 4° to 5° C. To the solution was added 1 mg of X-rich crystals of fenvalerate obtained in Example 1, and the resulting solution was stirred for 5 hours at the same temperature. The precipitated crystals were removed by filtration, and the mother liquor was concentrated to give 50.79 g of a Y-rich (X-isomer/Y-isomer=34.4/65.6).

EXAMPLE 9

The same procedure as in Example 8 was repeated except that a mixed solvent comprising 130 g of heptane and 70 g of methanol was used. Thus, 39.29 g of a Y-rich (X-isomer/Y-isomer=28.8/71.2) was obtained.

EXAMPLE 10

This example is explained by reference to the FIGURE.

1 g of X-rich crystals of fenvalerate (X-isomer/Y-isomer=88.1/11.9) were melted and then solidified on the inner surface of a tubular glass vessel 1 having an inlet 5 and an outlet 6 (inside diameter: about 36 mm) up to the level of 130 mm from the bottom. The vessel was placed in a bath 2 kept at −15° C. such that the area where the X-rich crystals were attached was dipped in the bath 2. Thereafter, a solution of 30 g of fenvalerate (X-isomer/Y-isomer=53.2/46.8) in 300 g of a methanol solution containing 1.5 g of acetic acid was circulated (flux: 2.8 ml/min) between the vessel 1 and a flask 3 equipped with a stirrer kept at room temperature (20°-23° C.) by means of a pump 4 for 2 days. Then, the resulting solution was concentrated to give 16.3 g of a Y-rich (X-isomer/Y-isomer=35.5/64.5).

EXAMPLE 11

10 g of a X-rich of fenvalerate (X-isomer/Y-isomer=65.1/34.9) was dissolved in 50 g of methanol. To the solution were added 100 g of soft glass beads having a diameter of 1 mm, and the system was heated under reflux condition for 2 hours. Thereafter, the system was cooled to room temperature (20°-23° C.), and the liquid portion was separated from the glass beads by decantation. Sampling a portion of the solution, it was analyzed by gas chromatography. As the result, it was found that the X-isomer/Y-isomer is 54.5/45.5, which proved that epimerization occurred.

This solution was cooled in a bath kept at −15° C., and after adding thereto a small amount of X-rich crystals, the resulting solution was allowed to stand for one day at the same temperature. During this procedure, crystals were found to gradually precipitate. Then, the solution was decanted and concentrated to give 2.23 g of a Y-rich (X-isomer/Y-isomer=17.0/83.0). The amount of the crystals thus precipitated was 7.28 g.

EXAMPLE 12

0.45 g of p-F fenvalerate (X-isomer/Y-isomer=53.4/46.6) was dissolved in 0.90 g of methanol, and the solution was cooled to about 0° C. To the solution was added a small amount of X-isomer crystals of p-F fenvalerate obtained in Reference Example 2, and the resulting solution was allowed to stand at the same temperature for 2 days. Thereafter, the precipitated crystals were collected by filtration to give 0.308 g of an X-rich (X-isomer/Y-isomer=62.3/37.7, m.p. 61.0° to 62.5° C.). The mother liquor was concentrated to give 0.141 g of a Y-rich (X-isomer/Y-isomer=32.7/67.3).

While the invention has been described in detail and with reference to specific embodiments thereof, it will be apparent to one skilled in the art that various changes and modifications can be made therein without departing from the spirit and scope thereof.

What is claimed is:

1. A method for preparing a mixture of stereoisomers of α-cyano-3-phenoxybenzyl isovalerate ester derivatives of the formula:

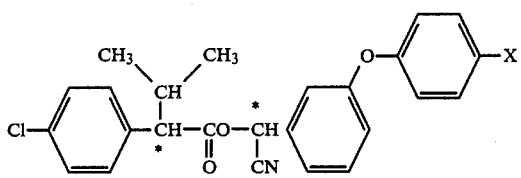

wherein X is a hydrogen atom or a fluorine atom, and * indicates an asymmetric carbon atom, which mixture is rich in a Y-isomer which is an enantiomer pair of a compound of said formula, one enantiomer having an (S)-configuration on both the acid and alcohol moieties and the enantiomer thereof having an (R)-configuration on both the acid and alcohol moieties, which method comprises removing crystals of a compound of said formula rich in an X-isomer which is an enantiomer pair of a compound of said formula, one enantiomer having an (S)-configuration on the acid moiety and an (R)-configuration on the alcohol moiety and the enantiomer thereof having an (R)-configuration on the acid moiety and an (S)-configuration on the alcohol moiety, from a mother liquor containing an ester of said formula which is a mixture of said X-isomer and said Y-isomer to obtain a mixture rich in said Y-isomer.

2. The method according to claim 1, which further comprises crystallizing the compound rich in said X-isomer before the removing step.

3. The method according to claim 1, which is carried out in a solvent.

4. The method according to claim 1, which is carried out in the presence of a crystalline X-isomer or a crystalline mixture of the ester rich in said X-isomer.

5. The method according to claim 1, wherein a crystalline X-isomer or a crystalline mixture of the ester rich in said X-isomer is added as a seed crystal.

6. The method according to claim 1, wherein a solidified mixture of said X-isomer and said Y-isomer is partially dissolved in a solvent and then, the solid is removed to obtain an ester rich in said Y-isomer from the solution.

7. The method according to claim 2, wherein the crystallization is carried out in a solvent.

8. The method according to claim 2, wherein the crystallization is carried out in the presence of a crystalline X-isomer or a crystalline mixture of the ester rich in said X-isomer.

9. The method according to claim 2, wherein a crystalline X-isomer or a crystalline mixture of the ester rich in said X-isomer is added as a seed crystal.

10. The method according to claim 3, which is carried out in the presence of a crystalline X-isomer or a crystalline mixture of the ester rich in said X-isomer.

11. The method according to claim 3, wherein a crystalline X-isomer or a crystalline mixture of the ester rich in said X-isomer is added as a seed crystal.

12. The method according to claim 7, wherein the crystallization is carried out in the presence of a crystalline X-isomer or a crystalline mixture of the ester rich in said X-isomer.

13. The method according to claim 7, wherein a crystalline X-isomer or a crystalline mixture of the ester rich in said X-isomer is added as a seed crystal.

14. The method according to claim 1, wherein said mixture of X-isomer and Y-isomer used as a starting material is prepared by removing crystals of a compound of said formula rich in an X-isomer from an ester of said formula which is a mixture of said X-isomer and said Y-isomer, and bringing the compound of said formula rich in an X-isomer into contact with a basic catalyst to induce epimerization thereof.

15. The method according to claim 2, wherein said mixture of X-isomer and Y-isomer used as a starting material is prepared by removing crystals of a compound of said formula rich in an X-isomer from an ester of said formula which is a mixture of said X-isomer and said Y-isomer, and bringing the compound of said formula rich in an X-isomer into contact with a basic catalyst to induce epimerization thereof.

16. The method according to claim 14, wherein the crystallization is carried out in the presence of a crystalline X-isomer or a crystalline mixture of the ester rich in said X-isomer.

17. The method according to claim 15, wherein a crystalline X-isomer or a crystalline mixture of the ester rich in said X-isomer is added as a seed crystal.

18. The method according to claim 1, 2, 3, 4, 5, 6, 7, 8, 9, 10, 11, 12, 13, 14, 15, 16 or 17 wherein a solvent selected from the group consisting of an alcohol, an aliphatic hydrocarbon, an alicyclic, hydrocarbon, a mixture of two or more of these solvents and a mixed solvent containing at least one of these solvents is used.

19. The method according to claim 1, 2, 3, 4, 5, 6, 7, 8, 9, 10, 11, 12, 13, 14, 15, 16 or 17, wherein X is a hydrogen atom.

20. The method according to claim 18, wherein said mixed solvent is a mixture of an aromatic hydrocarbon and a solvent selected from the group consisting of an alcohol, an aliphatic hydrocarbon, an alicyclic hydrocarbon and a mixture of two or more of these solvents.

21. The method according to claim 18, wherein said alcohol is a lower alcohol having 1 to 4 carbon atoms.

22. The method according to claim 20, wherein said alcohol is a lower alcohol having 1 to 4 carbon atoms.

23. The method according to claim 18, wherein X is a hydrogen atom.

24. The method according to claim 20, wherein X is a hydrogen atom.

25. The method according to claim 21, wherein X is a hydrogen atom.

26. The method according to claim 22, wherein X is a hydrogen atom.

27. A crystalline-form mixture of stereo-isomers of α-cyano-3-phenoxybenzyl isovalerate ester derivatives of the formula:

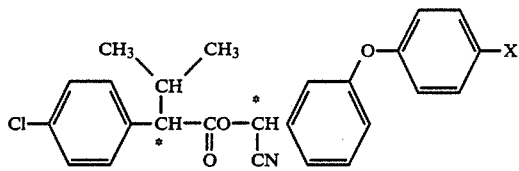

wherein X is a hydrogen atom or a fluorine atom, and * indicates an asymmetric carbon atom, which contains at least 60% of an enantiomer pair of a compound of said formula, one enantiomer having an (S)-configuration on the acid moiety and an (R)-configuration on the alcohol moiety and the enantiomer thereof having an (R)-configuration on the acid moiety and an (S)-configuration on the alcohol moiety.

28. A crystalline-form enantiomer pair of stereoisomers of a α-cyano-3-phenoxybenzyl isovalerate ester derivatives of the formula:

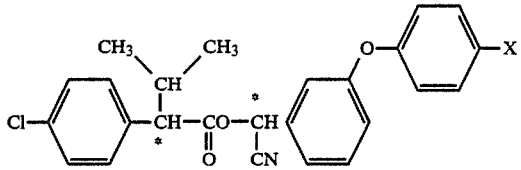

wherein X is a hydrogen atom or a fluorine atom, and * indicates an asymmetric carbon atom, which comprises an enantiomer pair of a compound of said formula, one enantiomer having an (S)-configuration on the acid moiety and an (R)-configuration on the alcohol moiety and the enantiomer thereof having an (R)-configuration on the acid moiety and an (S)-configuration on the alcohol moiety, substantially free of other stereoisomers of said ester derivative.

29. The crystalline-form mixture according to claim 27, wherein X is a hydrogen atom.

30. The crystalline-form enantiomer pair according to claim 28, wherein X is a hydrogen atom.

31. A method for preparation of a mixture of stereoisomers of α-cyano-3-phenoxybenzyl isovalerate ester derivatives of the formula:

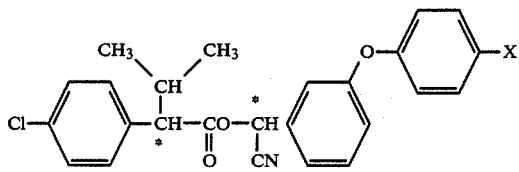

wherein X is a hydrogen atom of a fluorine atom, and * indicates an asymmetric carbon atom, which mixture is rich in a Y-isomer which is an enantiomer pair of a compound of said formula, one enantiomer having an (S)-configuration on both the acid and alcohol moieties and the enantiomer thereof having an (R)-configuration on both the acid and alcohol moieties, which method comprises partially dissolving a solidified mixture of said Y-isomer and an X-isomer which is an enantiomer pair of a compound of said formula having an (S)-configuration on the acid moiety and an (R)-configuration on the alcohol moiety and an enantiomer thereof having an (R)-configuration on the acid moiety and an (S)-configuration on the alcohol moiety in a solvent which preferentially dissolves said Y-isomer and then removing the remaining solid to obtain a solution rich in said Y-isomer.

32. The crystalline-form mixture according to claim 27, containing at least 70% of said enantiomer pair.

33. A method for preparation of a mixture of stereoisomers α-cyano-3-phenoxybenzyl isovalerate ester derivatives of the formula:

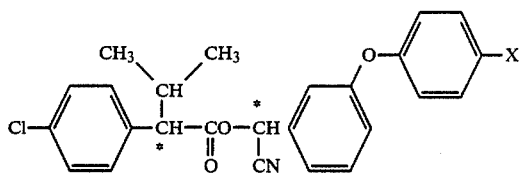

wherein X is a hydrogen atom or a fluorine atom, and * indicates an asymmetric carbon atom, which mixture is rich in a Y-isomer which is an enantiomer pair of a compound of said formula, one enantiomer having an (S)-configuration on both the acid and alcohol moieties and the enantiomer thereof having an (R)-configuration on both the acid and alcohol moieties which method comprises the steps of:

(a) removing crystals of a compound of said formula rich in an X-isomer which is an enantiomer pair of a compound of said formula, one enantiomer having an (S)-configuration on the acid moiety and an (R)-configuration on the alcohol moiety and the enantiomer thereof having an (R)-configuration on the acid moiety and an (S)-configuration on the alcohol moiety, from a mother liquor containing an ester of said formula which is a mixture of said X-isomer and said Y-isomer to obtain a mixture rich in said Y-isomer;

(b) separating said crystals of X-isomer from said mixture rich in said Y-isomer;

(c) bringing said separated X-isomer into contact with a basic catalyst to induce epimerization thereof to produce a mixture of X-isomer and Y-isomer; and (d) recycling the mixture of X-isomer and Y-isomer obtained in step (c) to the mother liquor of step (a).

34. The method of claim 33, wherein X is a hydrogen atom.

* * * * *